(12) United States Patent
Greer et al.

(10) Patent No.: US 9,492,239 B2
(45) Date of Patent: Nov. 15, 2016

(54) DEVICES FOR INTERFACING BETWEEN MANIPULATORS AND SURGICAL TOOLS

(76) Inventors: Alexander Greer, Calgary (CA);
Garnette Sutherland, Calgary (CA);
Tim Fielding, Brampton (CA)

( * ) Notice: Subject to any disclaimer, the term of this patent is extended or adjusted under 35 U.S.C. 154(b) by 526 days.

(21) Appl. No.: 12/596,420

(22) PCT Filed: Apr. 16, 2008

(86) PCT No.: PCT/IB2008/003465
§ 371 (c)(1),
(2), (4) Date: Jul. 16, 2010

(87) PCT Pub. No.: WO2009/027848
PCT Pub. Date: Mar. 5, 2009

(65) Prior Publication Data
US 2010/0286669 A1    Nov. 11, 2010

Related U.S. Application Data

(60) Provisional application No. 60/912,153, filed on Apr. 16, 2007.

(51) Int. Cl.
*A61B 17/00* (2006.01)

(52) U.S. Cl.
CPC .............. *A61B 34/30* (2016.02); *A61B 34/70* (2016.02); *A61B 2017/00477* (2013.01); *A61B 2034/305* (2016.02)

(58) Field of Classification Search
CPC ...................................................... A61B 19/22
USPC ............................................................ 606/1
See application file for complete search history.

(56) References Cited

U.S. PATENT DOCUMENTS

| | | | |
|---|---|---|---|
| 4,647,099 A | 3/1987 | Berry et al. | 294/103.1 |
| 5,413,573 A | 5/1995 | Koivukangas | 606/1 |
| 5,871,448 A | 2/1999 | Ellard | 600/459 |
| 6,451,027 B1 | 9/2002 | Cooper et al. | 606/130 |
| 7,155,316 B2 | 12/2006 | Sutherland et al. | 700/248 |
| 7,331,967 B2 | 2/2008 | Lee et al. | 606/130 |
| 2002/0120211 A1 | 8/2002 | Wardle et al. | 600/564 |
| 2003/0183545 A1 | 10/2003 | Lauryssen et al. | 206/364 |

(Continued)

FOREIGN PATENT DOCUMENTS

| | | |
|---|---|---|
| CA | 2 437 286 | 4/2008 |
| WO | WO 97/04713 | 2/1997 |

(Continued)

OTHER PUBLICATIONS

International Search Report and Written Opinion issued in PCT/IB2008/003465, dated May 27, 2009.

(Continued)

*Primary Examiner* — William Thomson
*Assistant Examiner* — John R Downey
(74) *Attorney, Agent, or Firm* — Norton Rose Fulbright US LLP

(57) ABSTRACT

A device, system and method for interfacing between an end effector of a manipulator and a surgical tool. Embodiments may include an upper tool holder element and a lower tool holder element. Embodiments may also include a drape between the end effector and the manipulator. Embodiments may also include two force sensors and a coupling arranged in a force sensor system for use with an end effector that includes a tool roll driver.

18 Claims, 20 Drawing Sheets

(56) References Cited

U.S. PATENT DOCUMENTS

| | | |
|---|---|---|
| 2003/0208187 A1 | 11/2003 | Layer .......................... 600/130 |
| 2004/0049205 A1* | 3/2004 | Lee et al. ..................... 606/130 |
| 2006/0161136 A1 | 7/2006 | Anderson et al. ........... 606/130 |
| 2006/0161137 A1 | 7/2006 | Orban, III et al. ........... 600/102 |
| 2007/0299427 A1* | 12/2007 | Yeung et al. .................... 606/1 |

FOREIGN PATENT DOCUMENTS

| | | |
|---|---|---|
| WO | WO 98/25666 | 6/1998 |
| WO | WO 98/56295 | 12/1998 |
| WO | WO 99/50721 | 10/1999 |
| WO | WO 02/062199 | 8/2002 |
| WO | WO 2004/014244 | 2/2004 |
| WO | WO 2004/084738 | 10/2004 |

OTHER PUBLICATIONS

Response to Office Action issued in European Patent Application No. 08828412.0-1269, dated Nov. 5, 2015.

\* cited by examiner

DEVICES FOR INTERFACING BETWEEN MANIPULATORS AND SURGICAL TOOLS

CROSS REFERENCE TO RELATED APPLICATIONS

This application is a national phase application under 35 U.S.C. §371 of International Application No. PCT/IB2008/003465, filed Apr. 16, 2008, which claims priority to U.S. Provisional Patent Application Ser. No. 60/912,153, filed Apr. 16, 2007, the entire contents of each of which are incorporated by reference.

BACKGROUND

The present devices relate generally to the field of surgical robotics, and more particularly to devices that interface between a manipulator (e.g., a surgical robotic arm) and a surgical tool. An example of a surgical robot with which the present devices can be used is disclosed in U.S. Pat. No. 7,155,316 (the "'316 patent"), which is incorporated by reference.

SUMMARY

The present devices can be used to interface between a manipulator, such as one of the surgical robotic arms disclosed in the '316 patent, and a surgical tool held by the manipulator. In some embodiments, the present devices include at least two tool holder elements, an upper element and a lower element, that are sterilizable, and that can reside outside of a sterile envelope created by a surgical drape. The terms "upper" and "lower" are used only for convenience and should be interpreted broadly to include other configurations (for example, elements that are laterally spaced). The elements can be made of MR-compatible materials. In some embodiments, the elements can also have one or more stabilizers that face inwardly from a given surface of the element and toward a surgical tool (when one is held by the device). The stabilizers can be biased (e.g., via springs) to contact and be pushed back by a tool (or tool adapter) to help keep the tool in a secure position. For the upper element shown in the figures, the stabilizers on the gate also serve as a means of biasing the gate to an open position following contact with a tool/tool adapter. For example, when a surgical tool is held by the upper element shown in the figures, and the latch of the upper element is depressed such that the gate is permitted to swing open, the stabilizers push off of the tool/tool adapter portion they are contacting and help cause the gate to swing open. In some embodiments, the lower element includes two separate arms that are pinned/hinged to a main portion, and that mate (e.g., via gears) to respective release projections (buttons), both of which must be depressed (in the depicted embodiment) in order to permit the arms to release the tool. One or both of the lower element arms can have a stabilizer to help hold a given tool more securely. The stabilizers may have any suitable biasing mechanism, such as the spring-loaded plungers shown in the figures.

The tool holder elements can be fastened to a manipulator (e.g., to an end effector of a manipulator) in any suitable fashion, such as with thumb screws. The screws may also pierce (or pass through pre-formed holes in) a sterilization drape to separate the sterilizable elements from the unsterilized components of the manipulator, thus helping to maintain the sterile barrier between the robot and patient. Each tool holder element may be cupped where it interfaces with the end effector so that it cups over the openings in the drape, which can also help to minimize the chance of contamination despite the break (via the drape openings) in the sterile barrier the drape creates.

Certain embodiments comprise a device for interfacing between an end effector of a manipulator and a surgical tool. In particular embodiments, the device comprises an upper tool holder element that includes a gate and a lower tool holder element. In certain embodiments, the upper tool holder element includes a latch that can secure the gate in a closed position. In particular embodiments, the latch is spring-biased. The upper tool holder element can be configured to surround a portion of a surgical tool when the gate is in a closed position and configured to expose a portion of the surgical tool when the gate is in the open position. The gate may include an inwardly-facing stabilizer in certain embodiments, and the inwardly-facing stabilizer may be spring-biased. In certain embodiments, the gate includes two inwardly-facing stabilizers, and each is spring-biased. In particular embodiments, the upper and lower tool holder elements include one or more fasteners for securing the upper and lower tool holder elements to an end effector of a manipulator. In specific embodiments, the one or more fasteners are configured to be removed from the upper and lower tool holder elements without the use of tools. The lower tool holder element includes two arms configured to partially surround a surgical tool in certain embodiments, and the lower tool holder may include a main portion, with each arm pinned to the main portion.

In certain embodiments, the lower tool holder element includes one release projection coupled to the first arm and another release projection coupled to the second arm. In specific embodiments, each release projection includes a geared portion that meshes with a geared portion of the arm to which that release projection is coupled. The release projections and the arms may be configured such that both release projections must be depressed in order to move the arms from a grasping to a non-grasping orientation. In certain embodiments, one of the arms includes an inwardly-facing stabilizer, and the inwardly-facing stabilizer may be spring-biased.

Particular embodiments may comprise a device for interfacing between an end effector of a manipulator and a surgical tool, where the device comprises: an upper tool holder element; a lower tool holder element separate from the upper tool holder element; and one or more fasteners configured to secure the upper and lower tool holder elements to an end effector of a manipulator. In certain embodiments, the one or more fasteners are configured to be removed from the upper and lower tool holder elements without the use of tools. In specific embodiments, the upper tool holder element includes a gate and a latch that can secure the gate in a closed position.

In certain embodiments the device for interfacing between an end effector of a manipulator and a surgical tool comprises: an upper tool holder element; a lower tool holder element including two arms configured to partially surround a surgical tool; and one release projection coupled to one of the arms and another release projection coupled to the other arm.

In particular embodiments, the device for interfacing between an end effector of a manipulator and a surgical tool comprises a sterilizable upper tool holder element; and a sterilizable lower tool holder element separate from the sterilizable upper tool holder element. In certain embodiments, the upper tool holder element includes one or more fasteners for securing the upper tool holder element to an end effector of a manipulator.

Particular embodiments comprise a system for interfacing between an end effector of a manipulator and a surgical tool. In specific embodiments, the system comprises a tool holder element configured for coupling to an end effector and a drape configured for placement between the tool holder element and an end effector. In certain embodiments, the tool holder element includes one or more fasteners configured to couple the tool holder element to an end effector. The one or more fasteners can be configured to contact the drape when the one or more fasteners are coupling the tool holder element to an end effector, in particular embodiments.

In certain embodiments, the one or more fasteners are configured to pierce the drape when the one or more fasteners are coupling the tool holder element to an end effector. In other embodiments, the one or more fasteners are configured to extend through one or more pre-existing holes in the drape when the one or more fasteners are coupling the tool holder element to an end effector. In particular embodiments, at least one of the one or more fasteners is configured to be inserted and removed from an end effector without the use of tools. In certain embodiments the drape may be transparent. The drape may be disposable in particular embodiments.

Other embodiments comprise a method of preparing an end effector. In certain embodiments, the method comprises: placing a drape over the end effector; engaging a tool holder element with the end effector; and securing the tool holder element to the end effector with one or more fasteners, where the one or more fasteners extend through the drape. In certain embodiments, at least one of the one or more fasteners pierce the drape. In particular embodiments, at least one of the one or more fasteners extend through pre-existing holes in the drape.

In certain embodiments comprising a device for interfacing between an end effector of a manipulator and a surgical tool, the device may comprise: an upper tool holder element; and a lower tool holder element separate from the upper tool holder element, the lower tool holder element including two separate arms.

Certain embodiments may comprise a method of preparing a slave manipulator for use in a surgical application. In specific embodiments, the method may comprise: placing a drape over the slave manipulator; securing a sterilized upper tool holder element to an end effector of the slave manipulator; securing a sterilized lower tool holder element to the end effector; and securing a surgical tool with the upper and lower tool holder elements by, at least in part, closing a gate of the upper tool holder element.

In particular embodiments, the drape can be positioned so that the tool roll drive shaft extends through a hole in the drape. The drape can be unrolled so that it extends over the manipulator, and the roll gear may then be placed on drive shaft and coupled with a fastener to secure the drape on the drive shaft. The upper tool holder element can be placed on an upper portion of the end effector and coupled with fasteners threaded into apertures. Similarly, the lower tool holder element may be coupled to the lower portion of the end effector with fasteners threaded into apertures. The drape can therefore be secured to the end effector with fasteners coupled to the drive shaft and the apertures in the end effector.

Some embodiments of the present devices comprise a force sensor system configured to interface between an end effector of a manipulator (such as a surgical robotic arm) and a tool holder device, that includes a first force sensor coupled to the end effector and to an upper tool holder, a coupling coupled to the end effector and a tool roll drive shaft, and a second force sensor coupled to the end effector and to a lower tool holder, where the coupling is configured to transmit rotational forces from the manipulator to the drive shaft. The coupling may be comprised of multiple pieces and flexible so as to avoid restricting the deformation of the force sensors, thereby enabling the first and second force sensors to sense the total actual forces on a tool coupled to the upper and lower tool holder elements. The force sensors and coupling may be located behind a sterile drape that separates the tool holder elements from the end effector. Further, the closest portion of each force sensor to the closest portion of a given tool holder (along a straight line) may be, for example, less than ten millimeters in some embodiments, and less than five millimeters in some embodiments.

Details associated with these embodiments and others are provided below.

Any embodiment of any of the present devices, systems, and methods may consist of or consist essentially of—rather than comprise/include/contain/have—the described features. Thus, in any of the claims, the term "consisting of" or "consisting essentially of" may be substituted for any of the open-ended linking verbs recited above, in order to change the scope of a given claim from what it would otherwise be using the open-ended linking verb.

BRIEF DESCRIPTION OF THE FIGURES

The following drawings illustrate by way of example and not limitation. Identical reference numerals do not necessarily indicate an identical structure. Rather, the same reference numeral may be used to indicate a similar feature or a feature with similar functionality. Every feature of each embodiment is not always labeled in every figure in which that embodiment appears, in order to keep the figures clear. The figures are drawn to scale, meaning the sizes of the depicted elements are accurate relative to each other for at least the depicted embodiments of the present devices and systems.

DESCRIPTION OF ILLUSTRATIVE EMBODIMENTS

Figure 1:
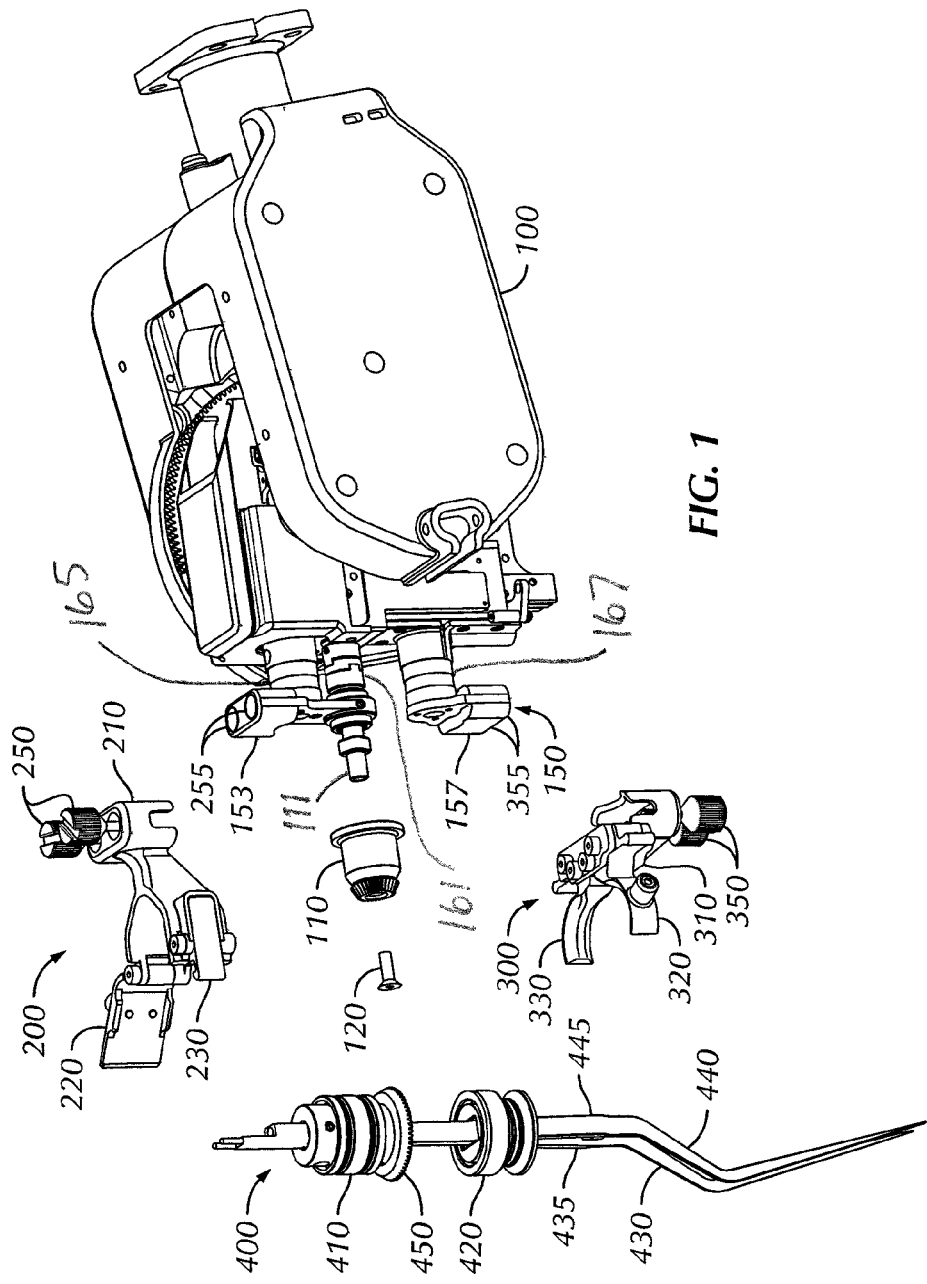
FIG. 1 illustrates an exploded view of a portion of a slave manipulator, an end effector, one embodiment of the present upper and lower tool holder elements, and a surgical tool.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. Thus, a device comprising certain elements and/or features includes at least those elements and/or features that are recited, but is not limited to possessing only the recited elements/features. Furthermore, a structure that is configured in a certain way must be configured in at least that way, but also may be configured in a way or ways that are not specified.

The terms "a" and "an" are defined as one or more than one, unless this application expressly requires otherwise. The term "another" is defined as at least a second or more.

Referring initially to the exemplary embodiment shown in FIGS. 1-5, manipulator portion 100 comprises an end effector 150 that can be used to hold a surgical tool 400 for positioning and manipulation by a slave manipulator of which manipulator portion 100 is a part. An upper tool holder element 200 and a lower tool holder element 300 provide an interface between end effector 150 and surgical tool 400. Upper tool holder element 200 is coupled to upper portion 153 of end effector 150 with fasteners 250 threaded into apertures 255, while lower tool holder element 300 is coupled to lower portion 157 of end effector 150 with fasteners 350 threaded into apertures 355 (which are not visible in FIG. 1, but are equivalent to apertures 255). Manipulator portion 100 may be configured such that lower portion 157 of end effector 150 is capable of moving away from upper portion 153 along, for example, a longitudinal rack in order to manipulate surgical tool 400, as discussed below.

Upper tool holder element 200 is configured to grasp an upper collar assembly 410 of surgical tool 400, while lower tool holder element 300 is configured to grasp a lower collar assembly 420 of surgical tool 400, which in the depicted embodiment is a pair of forceps. Upper and lower collar assemblies 410, 420 extend around a pair of forcep arms 430, 440 having ramp surfaces 435, 445, respectively. The upper and lower collar assemblies may be configured to fit a variety of instruments (e.g., surgical tools), such as bipolar surgical tools (such as the bipolar forceps that are shown in the figures), biopsy tools, guidewires, catheters, microscissors, suctions tools, forceps, dissectors, and needle drivers. Forcep arms 430, 440 are normally biased apart due to the configuration of forceps 400, but can be brought closer together by moving lower collar assembly 420 along ramp surfaces 435, 445. In this manner, forcep arms 430, 440 can be opened or closed when end effector 150 adjusts the position of lower collar assembly 420 relative to upper collar assembly 410.

End effector 150 also includes toll roll drive shaft 111 and a roll gear 110, which is coupled to drive shaft 111 with a fastener 120 such as a bolt or other coupling mechanism. In the embodiment shown, roll gear 110 engages a bevel gear 450 on surgical tool 400, so that roll gear 110 can rotate or roll surgical tool 400 about its primary longitudinal axis (i.e., the axis extending through the centers of upper and lower collar assemblies 410, 420).

Figure 2:
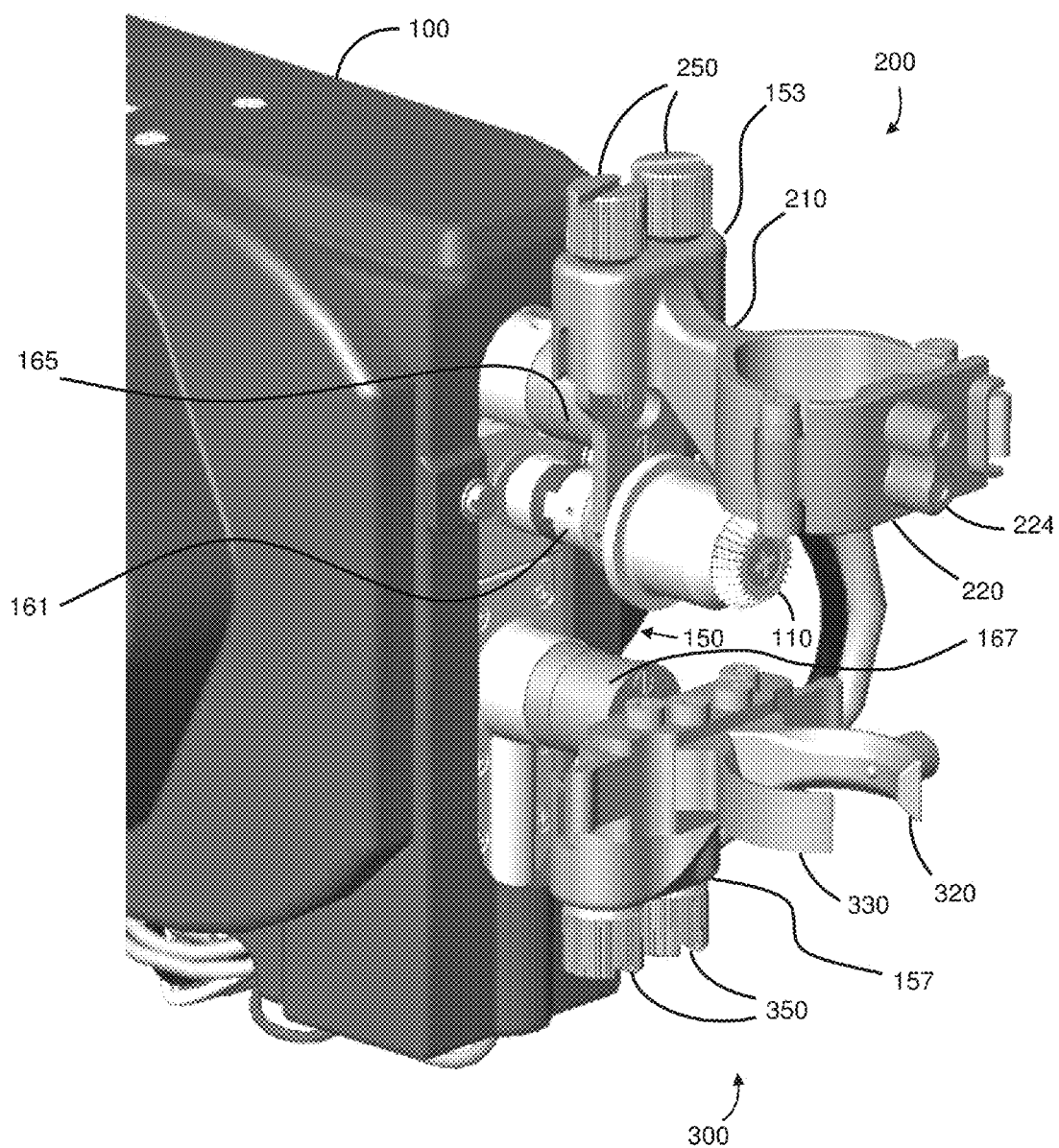
FIG. 2 depicts a perspective assembly view of the manipulator portion, end effector, upper tool holder element, and lower tool holder element illustrated in FIG. 1, with the upper and lower tool holder elements in the closed position.
Figure 3:
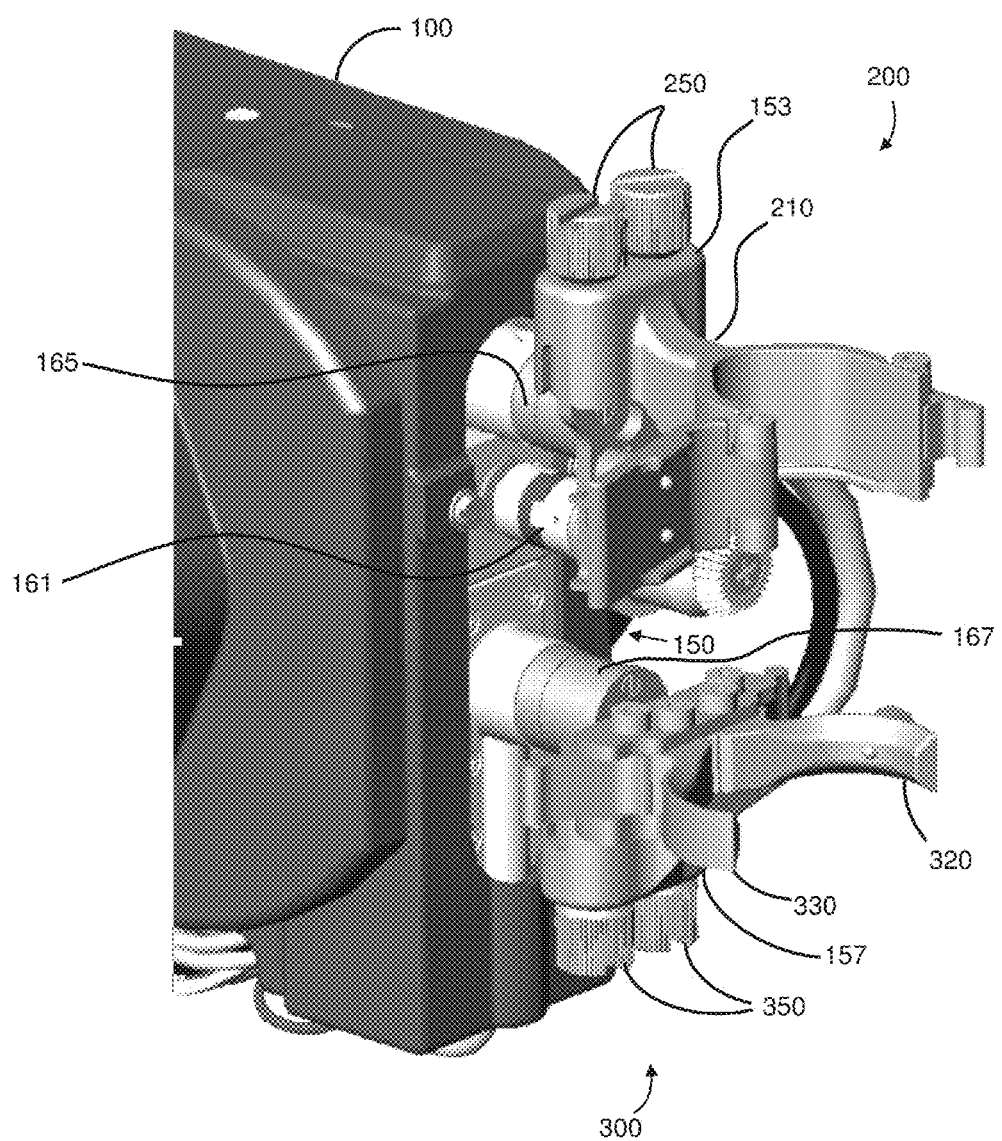
FIG. 3 depicts a perspective assembly view of the manipulator portion, end effector, upper tool holder element, and lower tool holder element illustrated in FIG. 1, with the upper and lower tool holder elements in the open position.
Figure 4A:
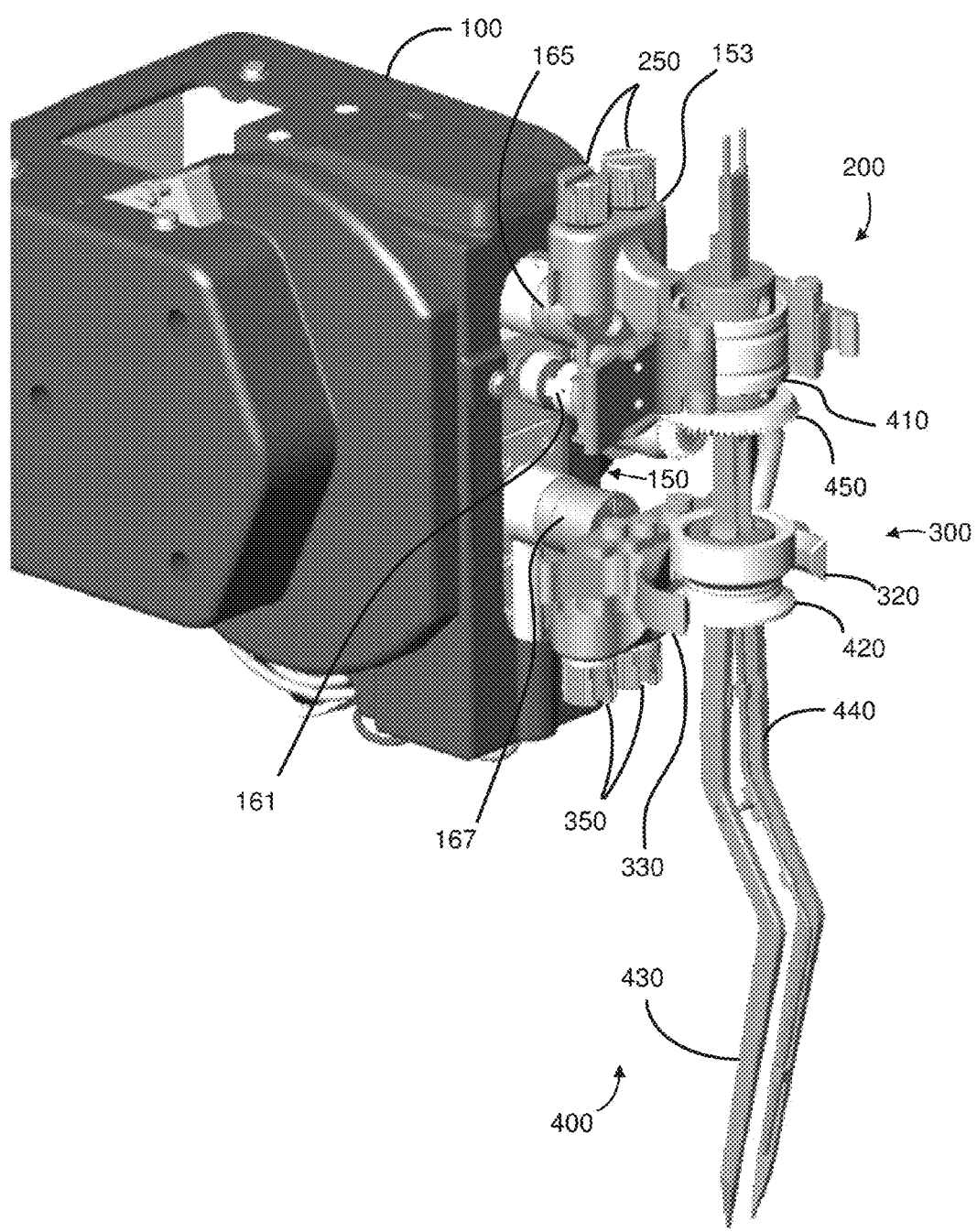
FIG. 4A depicts a perspective assembly view of the manipulator portion, end effector, upper tool holder element, lower tool holder element, and surgical tool illustrated in FIG. 1, with the upper and lower tool holder elements in the open position and the surgical tool positioned in the upper and lower tool holder elements.
Figure 4B:
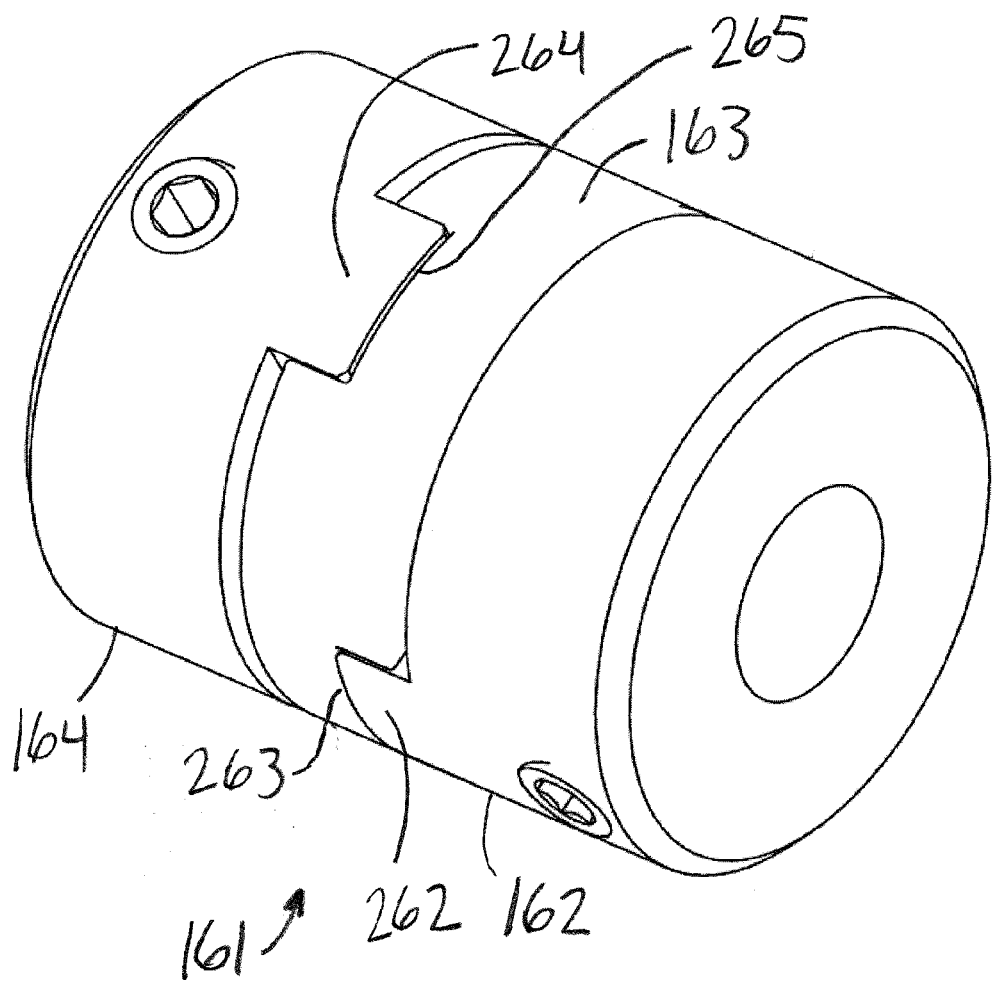
FIG. 4B depicts a perspective view of a coupling illustrated in FIG. 1.
Figure 5:
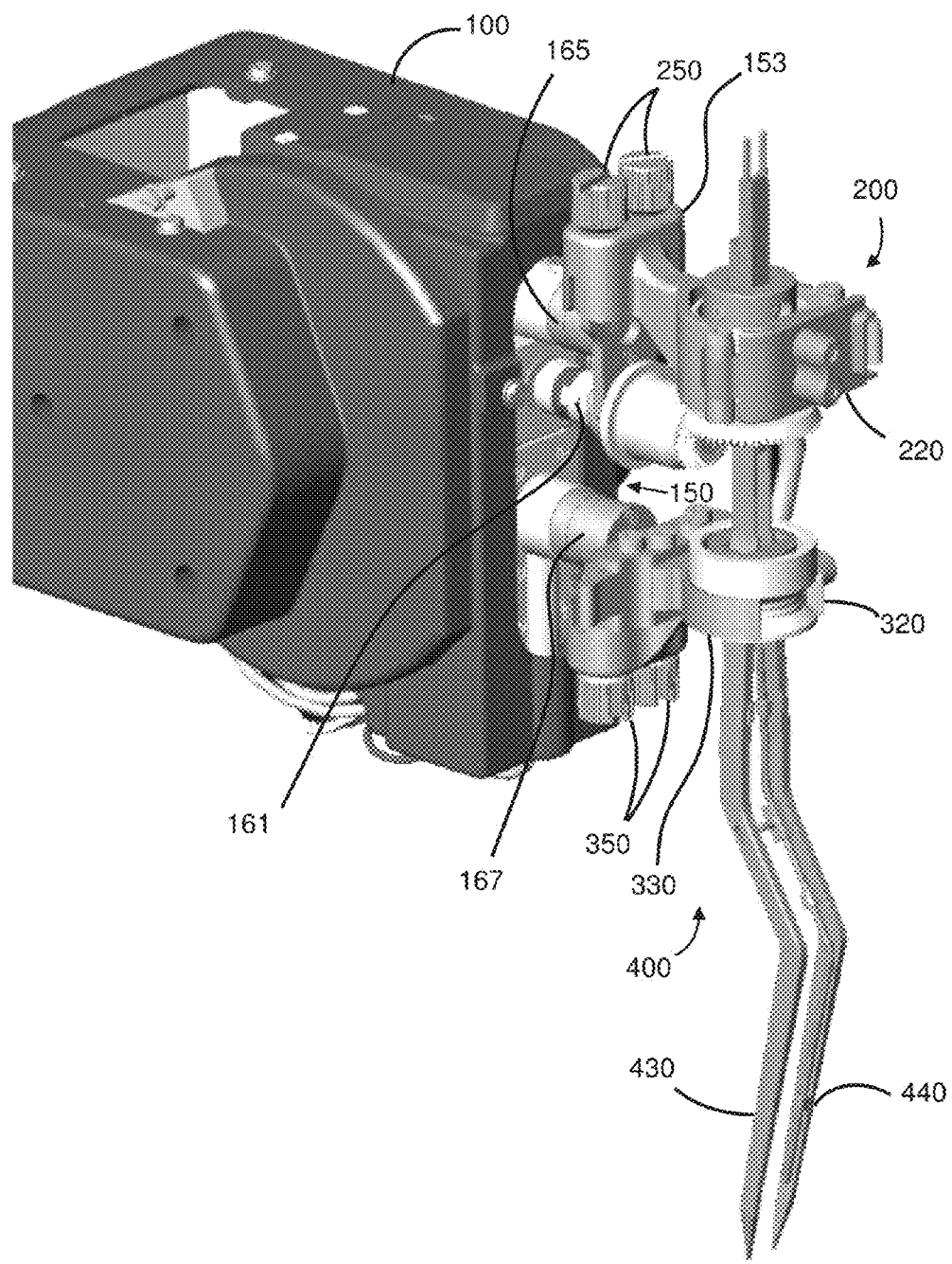
FIG. 5 depicts a perspective assembly view of the manipulator portion, end effector, upper tool holder element, lower tool holder element, and surgical tool illustrated in FIG. 1, with the surgical tool positioned in the upper and lower tool holder elements and the upper and lower tool holder elements in the closed position.

Upper tool holder element 200 comprises a body portion 210 with a gate 220 hingedly coupled to the body portion 210 and capable of moving from an open position (see FIGS. 1, 3, and 4) to a closed position (see FIGS. 2 and 5). In addition, lower tool holder element 300 comprises a main portion 310 and a pair of arms 320 and 330 capable of moving from an open position (see FIGS. 1, 3, and 4A) to a closed position (see FIGS. 2 and 5). As shown in FIG. 4A, upper collar assembly 410 can be inserted into upper tool holder element 200, while lower collar assembly 420 can be inserted into lower tool holder element 300 (when the collar assemblies are in the open position). After surgical tool 400 has been positioned as shown in FIG. 4A, gate 220 can be closed so that upper tool holder element surrounds upper collar assembly 410 of surgical tool 400, as shown FIG. 5. Arms 320, 330 can also be closed to a grasping position so that they partially surround lower collar assembly 420 of surgical tool 400 as shown in FIG. 5.

As shown the embodiment in FIGS. 1-4B, an upper (or first) force sensor 165 is positioned between upper portion 153 and manipulator 100, and a lower (or second) force sensor 167 is positioned between lower portion 157 and manipulator 100. In certain embodiments, force sensors 165, 167 can be used to provide force feedback to an operator of manipulator 100 through an input device, such as a hand controller that includes a stylus. In addition, a coupling 161 is positioned between drive shaft 111 and manipulator 100. In certain embodiments, coupling 161 is a flexible coupling that is configured to transmit rotational forces from manipulator 100 to drive shaft 111 without restricting the flexing motion of the sensors, which can then be interpreted by the sensors as forces.

A more detailed view of coupling 161 is provided in FIG. 4B. As seen in this view, coupling 161 comprises a first portion 164 that is coupled to a manipulator shaft (not visible in the figures) and a second portion 162 that is coupled to drive shaft 111. Coupling 161 also comprises a central portion 163 positioned between first portion 164 and second portion 162. In exemplary embodiments, central portion 163 is configured to allow some bending about the longitudinal axis of the tool roll drive shaft between first portion 164 and second portion 162, without causing bending forces between first portion 164 and second portion 162. In the specific embodiment shown, central portion 163 comprises slots (or recesses) 265 and 263 that receive tabs 264 and 262 from first and second portions 164, 162. Coupling 161 is configured so that tabs 264 and 262 can slide axially or translationally (due to bending) relative to slots 265 and 263 without transmitting axial or translational forces between first portion 164 and second portion 162. In exemplary embodiments, the primary axes of the manipulator shaft and drive shaft 111 are co-linear so that translational movement does not occur between first portion 164 and second portion 162.

As described above, non-rotational forces (e.g., axial and translational forces) are not transmitted between drive shaft 111 and manipulator 100. Therefore, force sensors 165 and 167 are able to detect the total axial and translational forces on tool 400. In certain embodiments, force sensors 165 and 167 are modified Nano17 Force/Torque sensors from ATI Industrial Automation. Specifically, force sensors 165 and 167 have been modified so that ferromagnetic materials have been removed and replaced with titanium components. In certain embodiments, force sensors 165 and 167 are 6-axis sensors that use multiple silicon strain gauges inside a cylindrical sensor. The data from the strain gauges can be sent through a calibration matrix that relates the combined voltages on the individual gauges to forces in X, Y and Z directions and torque values in yaw/pitch/roll orientations. In certain embodiments, only the X, Y and Z forces are analyzed. The force values on end effector 150 can be summed for X, Y and Z directions by summing the forces measured on the sensors 165, 167 because they are the two force carrying points of contact between tool 400 and manipulator 100. With only two points of contact, any forces exerted by the tool 400 should be transmitted through sensors 165, 167. In certain embodiments, the mass of the tool and tool holders can be compensated for (through gravity compensation) so that only the forces exerted on the tip of tool 400 are being fed back to hand controllers (not shown) of manipulator 100.

Referring now to FIGS. 6-14, a more detailed view and discussion of upper tool holder element 200 and its components is provided. During use, upper tool holder element 200 can be secured to end effector 150 via fasteners 250. In certain embodiments, fasteners 250 are configured so that they can be secured to or removed from end effector 150 without the use of other tools. For example, fasteners 250 may comprise an outer surface that is sized large enough and textured to allow a user to install fasteners 250 directly by hand and without the use of tools.

Figure 6:
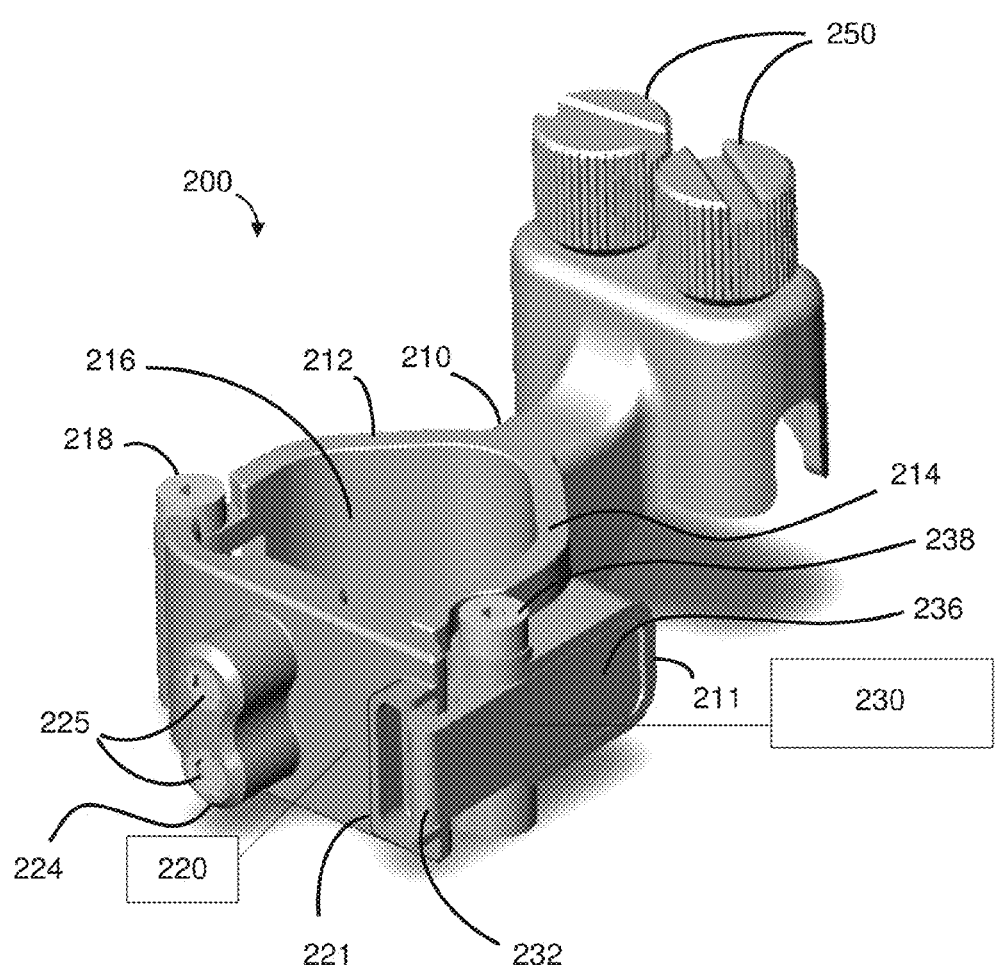
FIG. 6 depicts a perspective assembly view of the upper tool holder element illustrated in FIG. 1.
Figure 7:
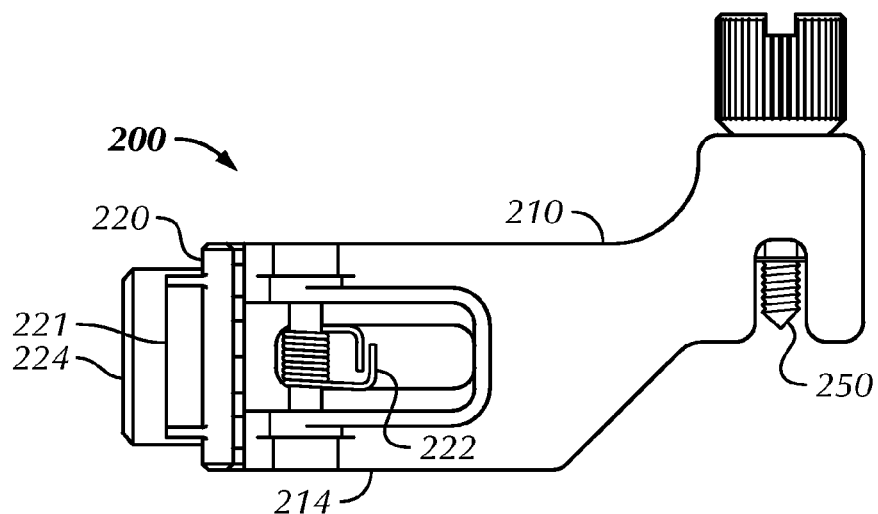
FIG. 7 depicts a side view of the upper tool holder element illustrated in FIG. 6 with the latch removed.
Figure 13:
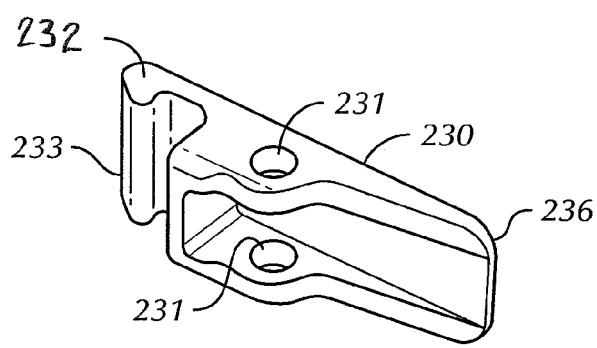
FIG. 13 depicts a perspective view of a latch of the upper tool holder element illustrated in FIG. 6.

As shown in the assembly view of FIG. 6, upper tool holder element 200 comprises a body portion 210 with a pair of fixed arms 212 and 214 that extend partially around an opening 216. A gate 220 (with a housing 224 and a pair of stabilizers 225) extends across opening 216 and is hingedly coupled to an end of arm 212 with a pin 218. A latch 230 is coupled to an end of arm 214 with a pin 238 in a manner that allows latch 230 to pivot or rotate about pin 238. FIG. 7 illustrates a side view of upper tool holder element 200 with latch 230 removed. In this view, a biasing member 222 is visible, which biases latch 230 towards a position that maintains gate 220 in a closed position. More specifically, biasing member 222 biases latch 230 so that an end 232 of latch 230 (shown in FIG. 8) is biased towards pin 218. In certain embodiments, biasing member 222 is a torsion spring. As shown in FIG. 13, end 232 comprises a hooked portion 233 for positively engaging latch 230 with gate 220.

Referring back now to FIG. 6, gate 220 is shown in the closed position. In order to move gate 220 to an open position, a user can push on latch 230 at an end 236 with a force sufficient to overcome the biasing force exerted by biasing member 222. This allows latch 230 to pivot or rotate about pin 238 so that end 232 is disengaged from gate 220. When end 232 is disengaged from gate 220, gate 220 can be moved to an open position. In certain embodiments, stabilizers 225 can bias gate 220 to an open position after latch 230 is released from gate 220. In certain embodiments, a user can provide the motive force to move gate 220 to an open position. In the embodiment shown, body portion 210 comprises a guard 211 to reduce the possibility that latch 230 could be accidentally manipulated to open gate 230. In addition, gate 220 comprises a guard 221 that reduces the possibility that end 232 of latch 230 could be unintentionally disengaged from gate 220.

As described above, when gate 220 is in an open position, surgical tool 400 can be positioned so that upper collar assembly 410 is located between arms 212 and 214 of body portion 210. When surgical tool 400 is so positioned, gate 220 can be moved to the closed position so that gate 200 and arms 212, 214 surround a portion of surgical tool 400 (for example, upper collar assembly 410).

Figure 8:
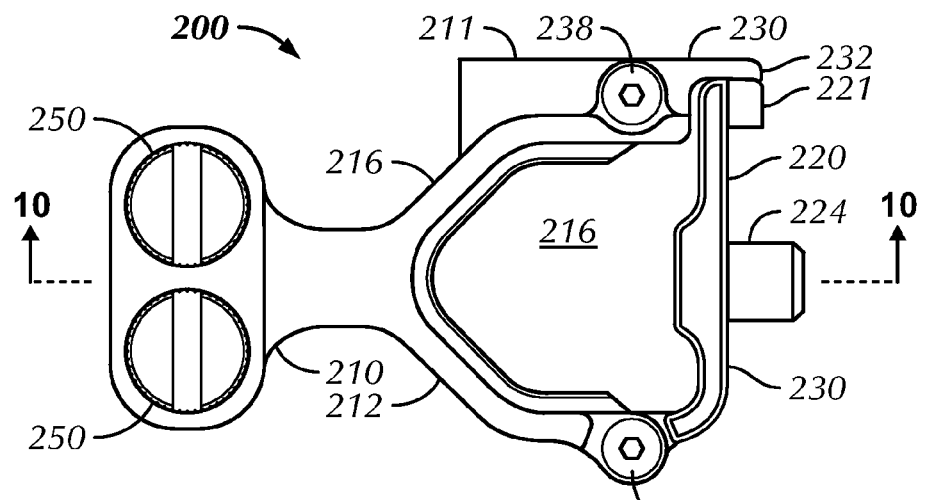
FIG. 8 depicts a top view of the upper tool holder element illustrated in FIG. 6.
Figure 9:
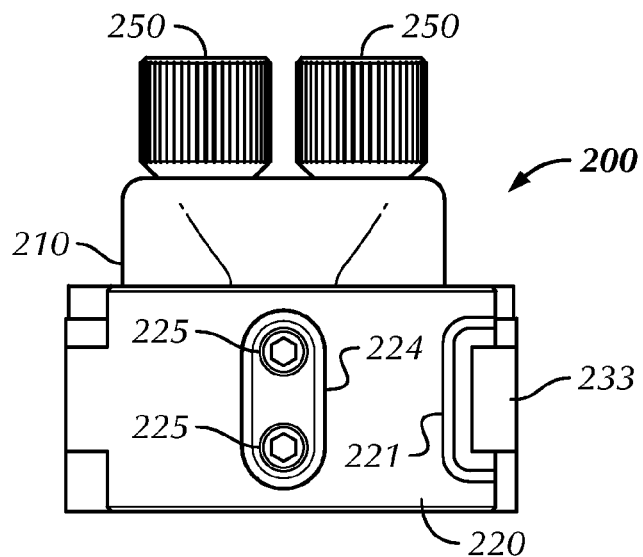
FIG. 9 depicts an end view of the upper tool holder element illustrated in FIG. 6.
Figure 10:
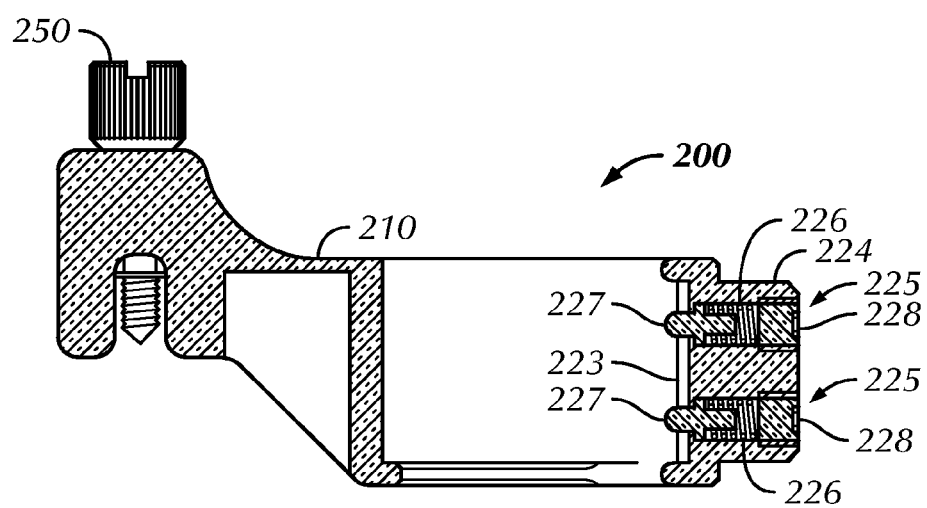
FIG. 10 depicts a section view of the upper tool holder element taken along line 10-10 in FIG. 8.

FIGS. 8 and 9 illustrate top and end views, respectively, of upper tool holder element 200. FIG. 10 illustrates a section view taken along line 10-10 of FIG. 8 and provides a more detailed view of stabilizers 225. In the section view of FIG. 10, stabilizers 225 comprise biasing members 226, plungers 227 and set screws 228. As shown, biasing members 226 bias plungers 227 to extend past the interior surface 223 of gate 220 into the opening 216. Stabilizers 225 are therefore capable of exerting a stabilizing force on upper collar assembly 410 when surgical tool 400 is installed in upper tool holder element 200. The exertion of a stabilizing force on surgical tool 400 can assist a user in maintaining control of surgical tool 400 during use. Stabilizers 225 can also minimize any movement of surgical tool 400 within upper tool holder element 200 due to any clearance between upper collar assembly 410 and opening 216.

Figure 11:
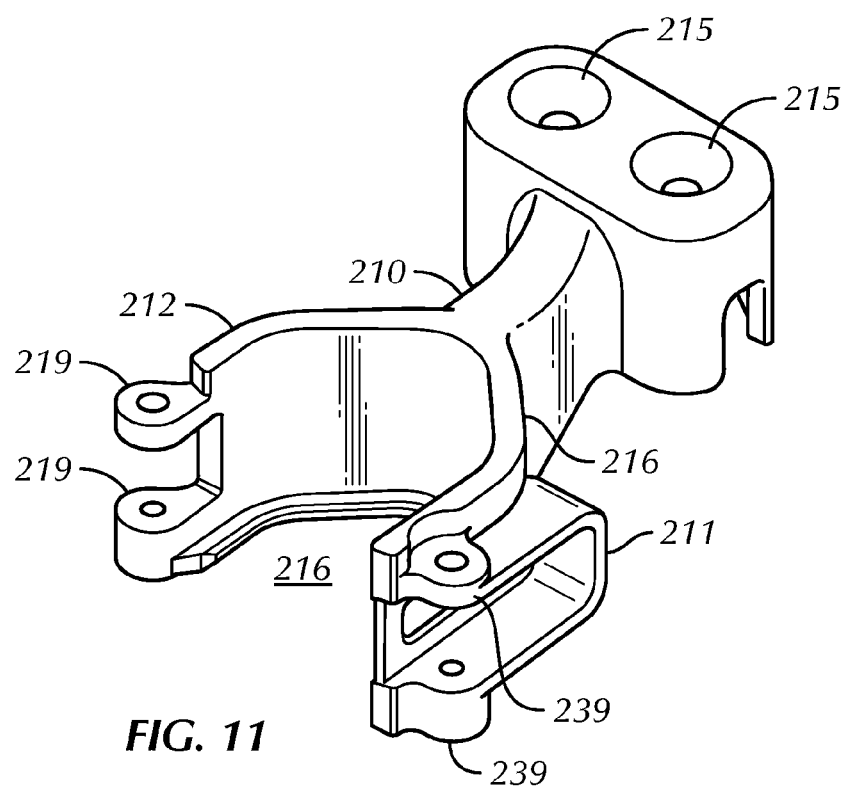
FIG. 11 depicts a perspective view of a body portion of the upper tool holder element illustrated in FIG. 6.
Figure 12:
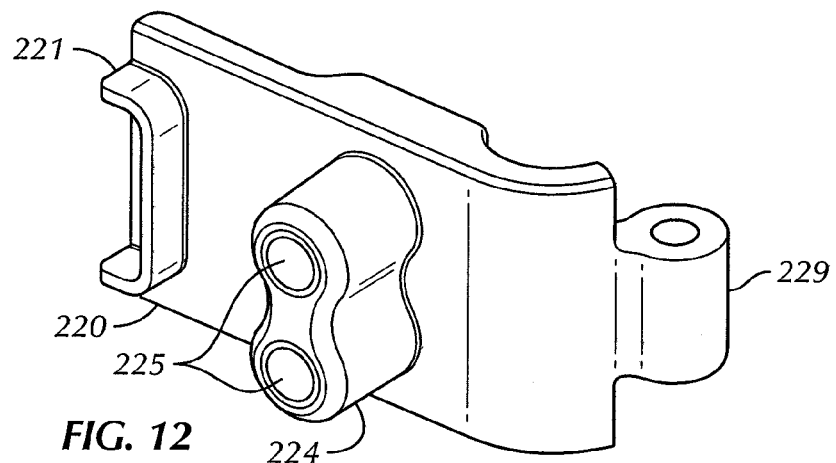
FIG. 12 depicts a perspective view of a gate of the upper tool holder element illustrated in FIG. 6.
Figure 14:
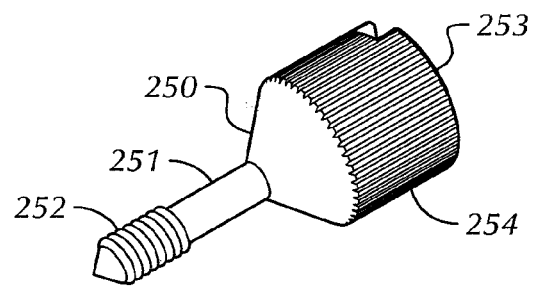
FIG. 14 depicts a perspective view of a fastener of the upper tool holder element illustrated in FIG. 6.

FIGS. 11-14 illustrate perspective views of individual components in upper tool holder element 200. Specifically, FIG. 11 illustrates a perspective view of body portion 210, FIG. 12 illustrates a perspective view of gate 220, FIG. 13 illustrates a perspective view of latch 230, and FIG. 14 illustrates a perspective view of fastener 250.

As shown in FIG. 11, body portion 210 comprises guard 211 that is configured to extend around latch 230 (not shown). Body portion 210 also comprises an outer hinge portion 219 configured to receive pin 218 and an outer hinge portion 239 configured to receive pin 238. Also visible in FIG. 11 are two openings 215 configured to receive fasteners 250.

As shown in FIG. 12, gate 220 comprises an inner hinge portion 229 configured to receive pin 218. Also visible in FIG. 12 are guard 221 and a housing 224 for stabilizers 225.

Referring now to FIG. 13, latch 230 comprises a pair of openings 231 configured to receive pin 238. Also visible in FIG. 13 is hooked portion 233 of end 232 opposite of end 236. As shown in FIG. 14, fastener 250 comprises a shaft 251 with a threaded portion 252 and a head portion 253 with ridges 254 that make it easier for a user to grip and install fastener 250. In addition, the threads on threaded portion 252 hold fastener 250 captive, so that it will not fall out of body portion 210 or opening 215.

Referring now to FIGS. 15-23, a more detailed view and discussion of lower tool holder element 300 and its components is provided. During use, lower tool holder element 300 can be secured to end effector 150 via fasteners 350, which are equivalent to fasteners 250 discussed above.

Figure 15:
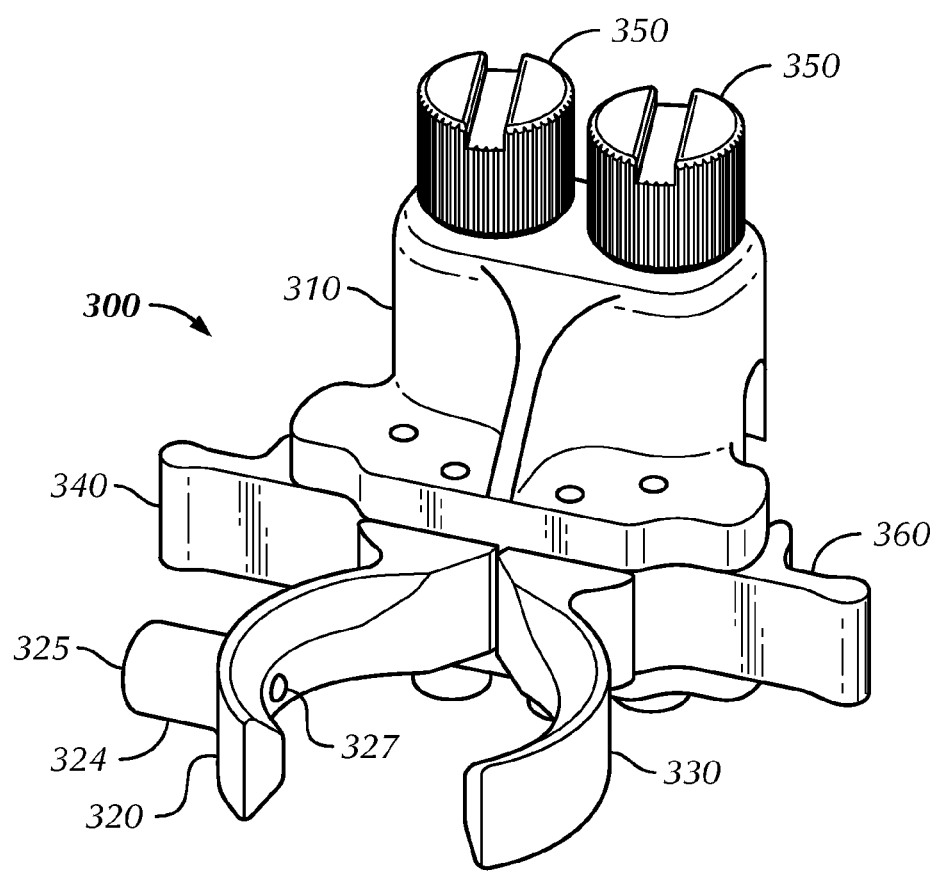
FIG. 15 depicts a perspective assembly view of the lower tool holder element illustrated in FIG. 1, where the lower tool holder element is in an inverted position as compared to that shown in FIG. 1.
Figure 16:
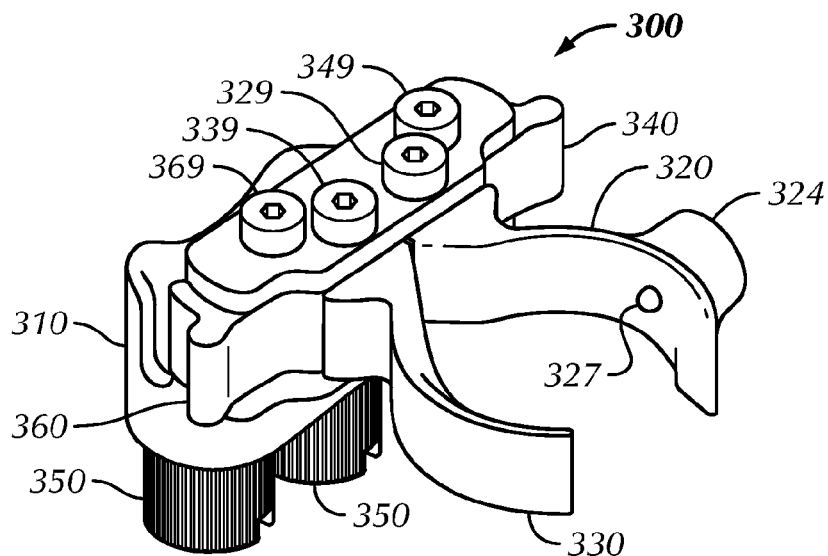
FIG. 16 depicts a perspective assembly view of the lower tool holder element illustrated in FIG. 1.
Figure 21:
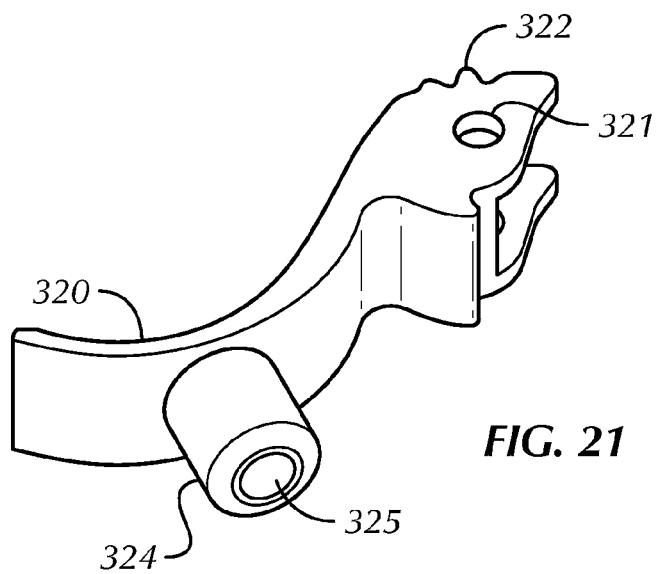
FIG. 21 depicts a perspective view of one arm of the upper tool holder element illustrated in FIG. 16.
Figure 22:
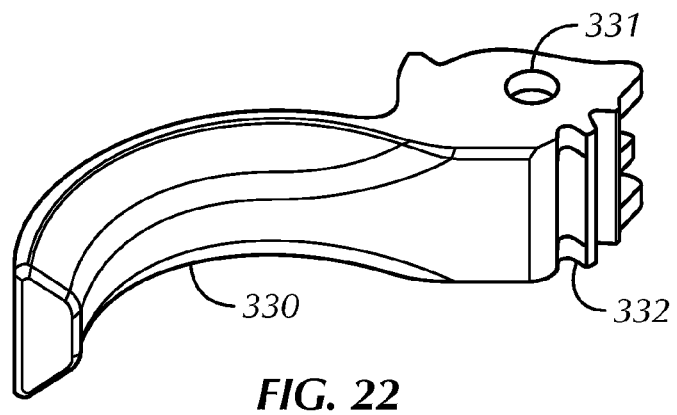
FIG. 22 depicts a perspective view of a second arm of the upper tool holder element illustrated in FIG. 16.
Figure 23:
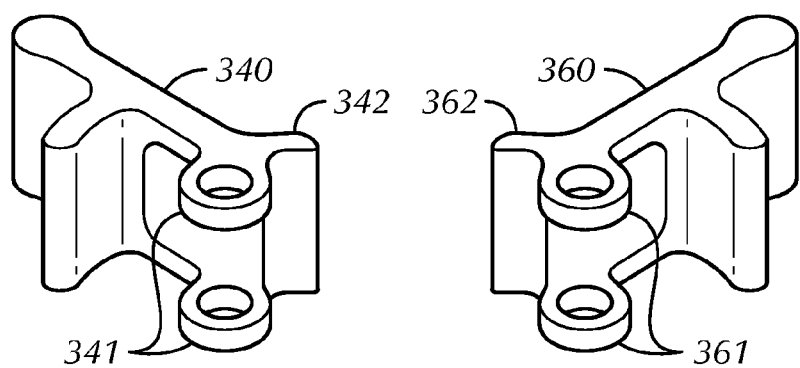
FIG. 23 depicts a perspective view of a pair of release projections of the upper tool holder element illustrated in FIG. 16.

As shown in the assembly view of FIG. 15, lower tool holder element 300 comprises main portion 310, a pair of arms 320 and 330, and a pair of release projections 340, 360. Arm 320 comprises a housing 324 for a stabilizer 325 with a plunger 327 that extends past the inner surface of arm 320. As explained below, release projections 340, 360 (which are pushed to open arms 320 and 330) can be manipulated so that arms 320, 330 move from a closed to an open position. As shown in FIGS. 21 and 22, arms 320 and 330 comprise apertures 321, 331 and geared portions 322, 332, respectively. As shown in FIG. 23, release projections 340, 360 comprise geared portions 342, 362 respectively. It is understood that geared portions 322, 332, 342 and 362 may comprise a single gear tooth. Also visible in FIG. 23, release projections 340, 360 comprise pivot members 341, 361 respectively. During operation, a user can open arms 320, 330 by pushing on release projections 340, 360 to rotate or pivot them about pins 349, 369 (visible in FIG. 16), which extend through pivot members 341, 361. As release projections 340, 360 rotate or pivot, geared portions 342, 362 engage and mesh with geared portions 322, 332 of arms 320, 330. Arms 320, 330 can then pivot about pins 329, 339 (visible in FIG. 16), which extend through apertures 321, 331 (shown in FIGS. 21 and 22, respectively) and apertures 336, 337 and 326, 327 (shown in FIG. 20). By pushing on release projections 340, 360, arms 320, 330 can move from the grasping position to the non-grasping position. To close arms 320, 330, a user can squeeze or pull arms 320, 330 together to a closed or grasping position. Projections 340, 360 can latch automatically when arms 320, 330 are pulled together. In certain embodiments, arms 320, 330 are biased open, and projections 340, 360 are biased closed. In such embodiments, when projections 340, 360 are pushed, arms 320, 330 pop open, and when projections 320, 330 are squeezed together, arms 340, 360 snap closed to a latched position.

When arms 320, 330 are in the non-grasping position, surgical tool 400 can be positioned so that lower collar assembly 420 is located within lower tool holder element 300. When lower collar assembly 420 is so positioned, a user can manipulate arms 320, 330 to move arms 320, 330 to the closed or grasping position. Arm 320 comprises a stabilizer 325 that is generally equivalent to stabilizers 225 discussed above. Stabilizer 325 can be used to stabilize lower collar assembly 420 within arms 320, 330 in the manner that stabilizer 225 stabilizes upper collar assembly 410 within space 216 of fixed arms 212, 214.

Figure 17:
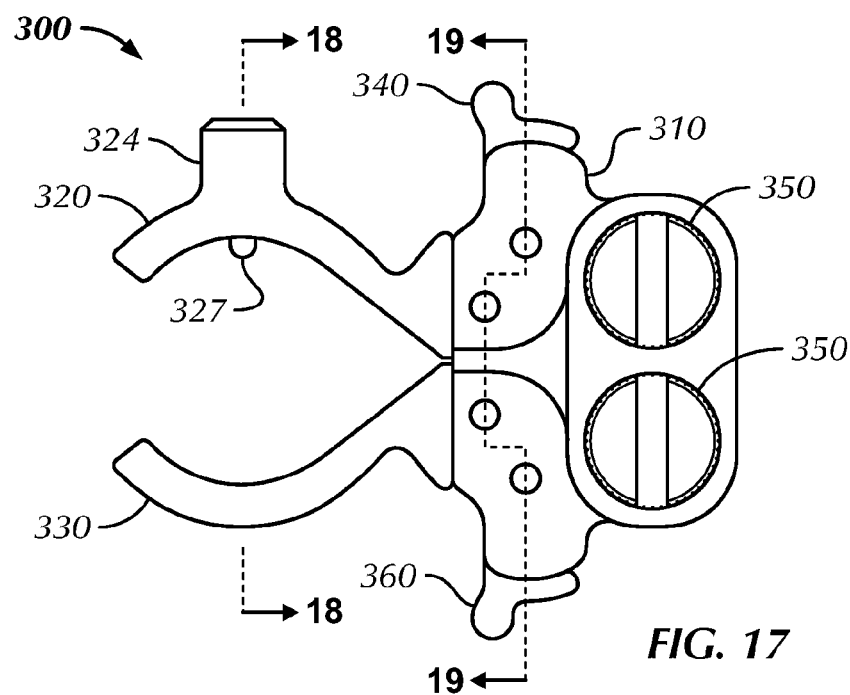
FIG. 17 depicts a bottom view of the lower tool holder element illustrated in FIG. 16.
Figure 18:
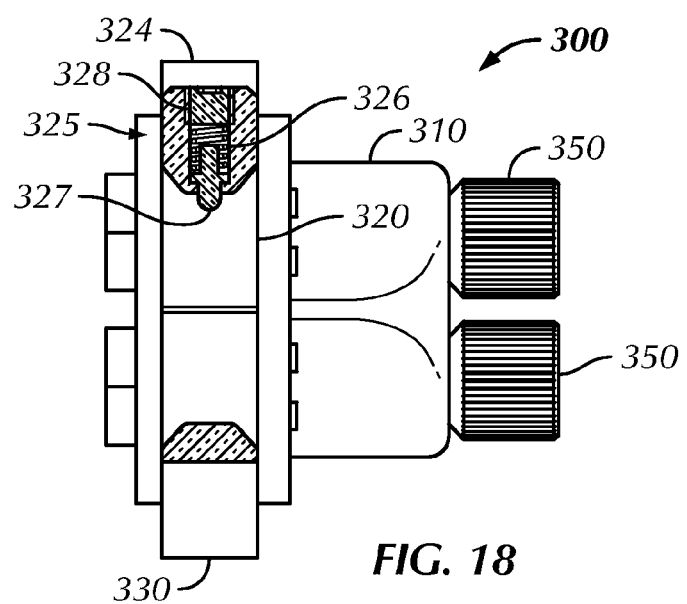
FIG. 18 depicts a section view of the lower tool holder element taken along line 18-18 in FIG. 17.

Referring now to FIG. 17, a bottom view of lower tool holder element 300 depicts arms 320, 330 in the closed position. A section view taken along line 18-18 is shown in FIG. 18. As shown in this view, stabilizer 325 comprises biasing member 326, plunger 327 and set screw 328.

Figure 19:
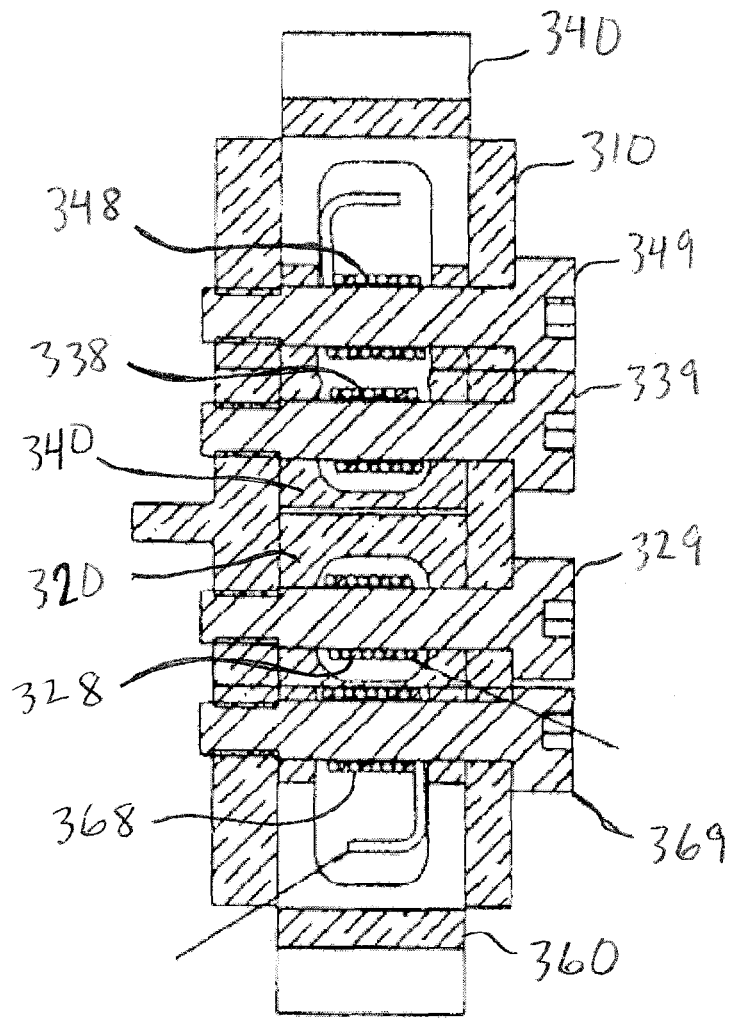
FIG. 19 depicts a section view of the lower tool holder element taken along line 19-19 in FIG. 17.

Referring now to FIG. 19, a section view taken along line 19-19 of FIG. 17 illustrates biasing members 328, 338, 348 and 368 disposed around pins 329, 339, 349 and 369. In certain embodiments, biasing members 328, 338, 348 and 368 are torsion springs that are configured to bias release projections 340, 360 to a latched closed position and arms 320, 330 to an open or non-grasping position.

Figure 20:
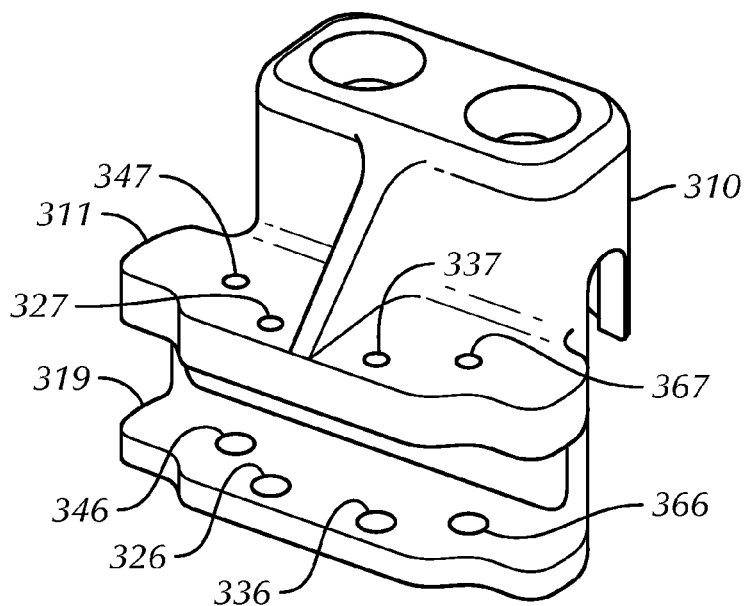
FIG. 20 depicts a perspective view of a main portion of the upper tool holder element illustrated in FIG. 16.

Referring now to FIG. 20, a perspective view of main portion 310 illustrates a first flanged portion 311 comprising openings 367, 327, 337 and 347 and a second flanged portion 319 comprising openings 366, 326, 336, and 346. Openings 367 and 366 are configured to receive pin 369, while openings 327 and 326 are configured to receive pin 329. In addition, openings 337 and 336 are configured to receive pin 339 and openings 347 and 346 are configured to receive pin 349.

Figure 24:
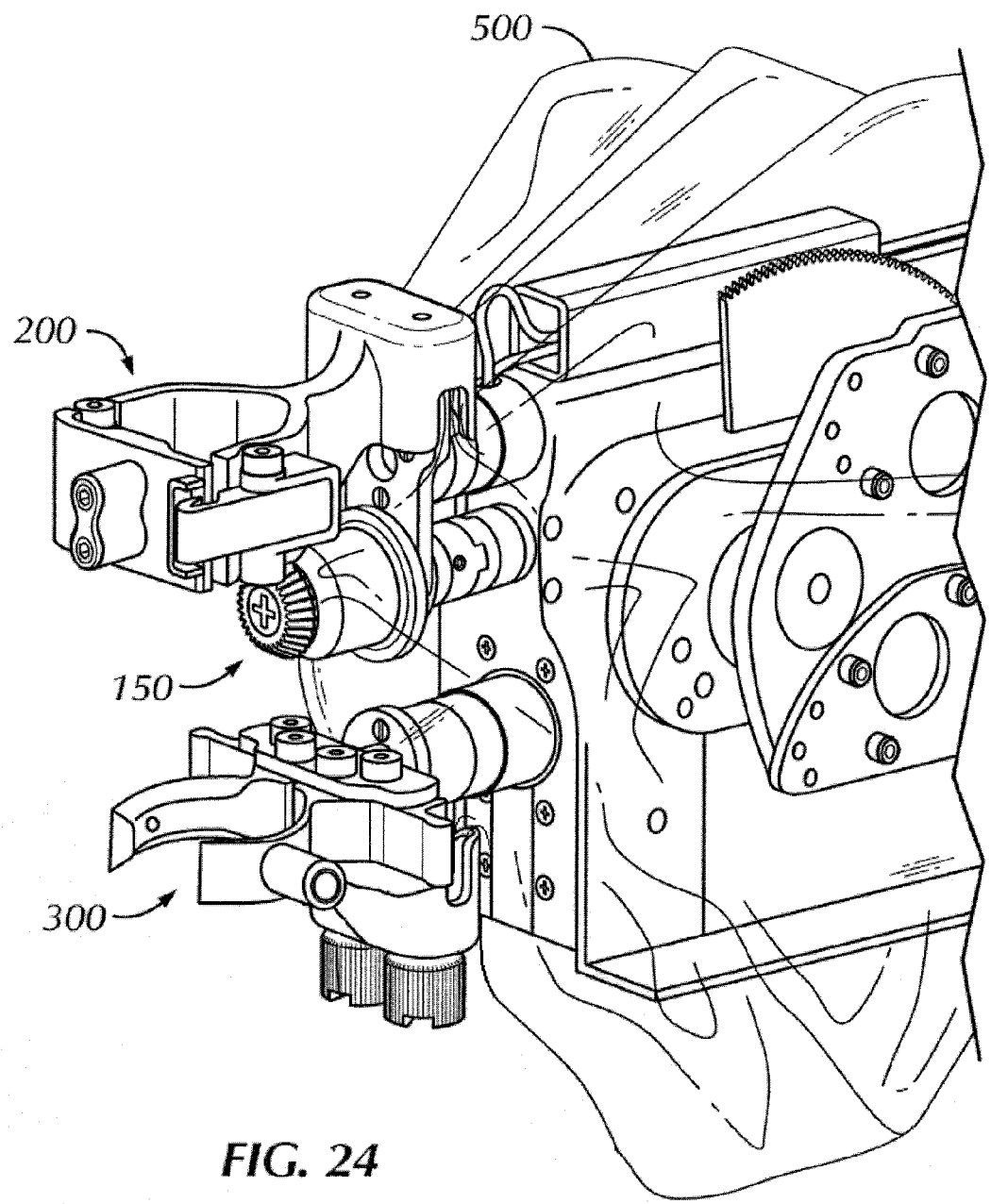
FIG. 24 depicts a perspective view of the manipulator, end effector, upper tool holder element, and lower tool holder element illustrated in FIG. 1, with a drape separating the manipulator and end effector from the upper and lower tool holder elements.
Figure 25:
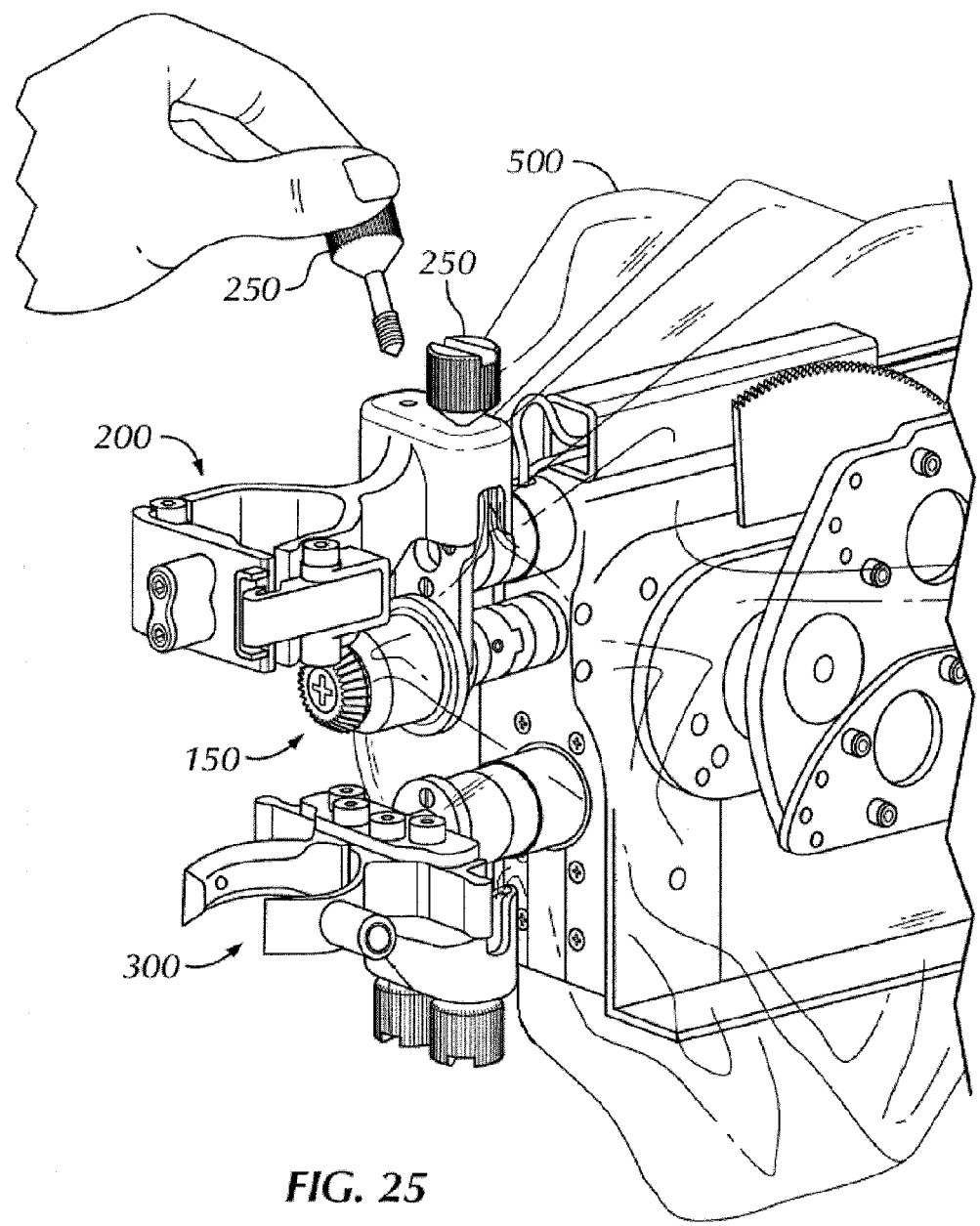
FIG. 25 depicts a perspective view of the manipulator portion, end effector, upper tool holder element, and lower tool holder element illustrated in FIG. 1, with a drape separating the manipulator and end effector from the upper and lower tool holder elements, and a fastener contacting the drape.

Referring now to FIGS. 24 and 25, a drape 500 is shown between end effector 150 and upper and lower tool holder elements 200, 300. Fasteners 250 (and 350, not shown) may be used to secure upper and lower tool holder elements 200, 300 to end effector 150 (specifically, upper portion 153 and lower portion 157). In certain embodiments, fasteners 250 and 350 may pierce drape 500 when they are threaded into end effector 150. In other embodiments, fasteners 250 and 350 may extend through pre-existing holes in drape 500 when they are threaded into end effector 150.

Drape 500 can provide a barrier between components that are sterilized (for example, upper and lower tool holder elements 200, 300 and surgical tool 400) and those components that are not sterilized (for example, end effector 150 and manipulator 100). Drape 500 can reduce the likelihood that a non-sterilized component can contaminate a surgical environment. In certain embodiments, drape 500 is transparent so that it does not restrict a user's visibility and allows the components underneath the drape to be visible. In certain embodiments, drape 500 is disposable so that it can be replaced after each use. Drape 500 may be comprised of polyethylene, vinyl, plastic or other suitable materials, and may have any suitable thickness, such as 0.05 millimeters.

Figure 26:
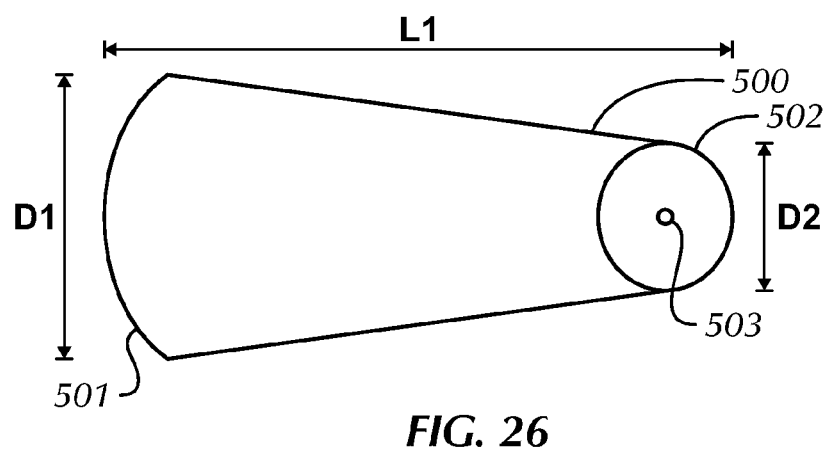
FIG. 26 depicts a schematic view of one embodiment of a drape.

FIG. 26 depicts a schematic view of one embodiment of drape 500. In this embodiment, drape 500 is generally a truncated cone shape and comprises an open end 501 and a closed end 502. In the specific embodiment shown, the length of drape 500 (represented by dimension L1 in FIG. 26) is approximately 1.5 meters long. In the embodiment shown, open end 501 is approximately 40 centimeters in diameter (represented by dimension D1) when end 501 is formed in a circle. In this embodiment, closed end 502 is approximately 20 centimeters in diameter (represented by dimension D2) when closed end 501 is formed in a circle. In the embodiment shown, closed end 502 comprises a hole 503 that can be placed over tool roll drive shaft 111. In specific embodiments, hole 503 is approximately 5 millimeters in diameter and is centered on closed end 502.

In certain embodiments, drape 500 can be positioned so that drive shaft 111 extends through hole 503. Drape 500 can then be unrolled so that it extends over manipulator portion 100 and remaining portions of the manipulator (not shown). Roll gear 110 may then be placed on drive shaft 111 and secured with fastener 120 to capture drape 500 on drive shaft 111. Upper tool holder element 200 may then be placed on upper portion 153 and coupled with fasteners 250 threaded into apertures 255. Similarly, lower tool holder element 300 may be coupled to lower portion 157 of end effector 150 with fasteners 350 threaded into apertures 355.

The present devices, including the upper and lower tool holders, can be made from any suitable material, including materials such as titanium, stainless steel alloys, and austenitic nickel-based superalloys (e.g., Inconel® alloys from Special Metals Corporation, Huntington, W.V.) that can be sterilized. A material that is sterilizable is defined as a material that becomes sterile after going through an approved method of sterilization without degrading. Examples of sterilization methods include the use of ethylene oxide gas, steam, autoclaves, and Sterrad® sterilization systems (from Advanced Sterilization Products, Irvine, Calif.). The material or materials chosen may also be magnetic resonance-compatible.

Descriptions of well known manufacturing and assembly techniques, components and equipment have been omitted so as not to unnecessarily obscure the present devices and systems in unnecessary detail. Further, the present devices and systems are not intended to be limited to the particular forms disclosed. Rather, they are to cover all modifications, equivalents, and alternatives falling within the scope of the claims.

For example, the upper and lower tool holders of the present devices may be configured differently than shown in the figures. In alternative embodiments, upper tool holder element 200 may comprise stabilizers 225 on body portion 210 rather than gate 220. Upper tool holder element may also comprise a two-piece gate that is hinged to body portion 210 at each end and latches in the middle. Alternative embodiments may also comprise a lower tool holder element 300 with arms 320 and 330 that extend completely, rather than partially, around an object when the arms are in a closed position.

The appended claims are not to be interpreted as including means-plus-function limitations, unless such a limitation is explicitly recited in a given claim using the phrase(s) "means for" and/or "step for," respectively.

The invention claimed is:

1. A device for interfacing between an end effector of a manipulator and a surgical tool having an upper collar assembly and a lower collar assembly, the device comprising:
   an upper tool holder element configured to grasp the upper collar assembly, the upper tool holder element comprising a body portion with a pair of fixed arms forming an opening therebetween, a gate hingedly coupled to an end of one of the pair of fixed arms, a biased latch pivotably coupled to the other of the pair of fixed arms for securing the gate in a closed position across the opening between the pair of fixed arms, and a biasing member for pivotably biasing the latch in the closed position; and
   a lower tool holder element configured to grasp the lower collar assembly; wherein the upper tool holder element and the lower tool holder element are configured for coupling to the end effector and the upper tool holder element is separate from the lower tool holder element; wherein the lower tool holder element is movable, thereby adjusting the lower collar assembly relative to the upper collar assembly; and
   wherein the gate is secured or released through pivotal motion of the latch, wherein the upper tool holder element is configured to surround a portion of the surgical tool when the gate is closed and configured to expose a portion of the surgical tool when the gate is open, and wherein the gate includes one or more inwardly-facing spring biased stabilizers, wherein each of said one or more stabilizers comprises a plunger, a spring biasing member for biasing the plunger to extend past an interior surface of the gate into the opening, and a set screw.

2. The device according to claim 1, wherein the latch is resiliently biased.

3. The device according to claim 1, wherein the lower tool holder element includes a main portion and two arms coupled to the main portion, the two arms configured to partially surround the surgical tool.

4. The device according to claim 3, wherein each arm is pinned to the main portion.

5. The device according to claim 3, wherein at least one of the arms includes an inwardly-facing stabilizer.

6. The device according to claim 5, wherein the inwardly-facing stabilizer is biased.

7. The device according to claim 1, wherein the lower tool holder element includes a main portion and two arms coupled to the main portion, the two arms configured to partially surround the surgical tool, and a first release projection coupled to the first arm and a second release projection coupled to the second arm, the release projections configured for moving the arms between a closed position and an open position.

8. The device according to claim 7, wherein each release projection includes a geared portion that meshes with a geared portion of the arm to which that release projection is coupled.

9. The device according to claim 7, wherein the release projections and the arms are configured such that both release projections must be depressed in order to move the arms from the closed to the open position.

10. The device according to claim 7, wherein at least one of the arms includes an inwardly-facing stabilizer.

11. The device according to claim 10, wherein the inwardly-facing stabilizer is biased.

12. The device according to claim 1, wherein the upper tool holder element and the lower tool holder element are sterilizable.

13. The device according to claim 1, further comprising one or more fasteners for securing the upper tool holder element and the lower tool holder element to the end effector.

14. The device according to claim 13, wherein the fasteners can be fastened and released without the use of tools.

15. The device according to claim 13, further comprising a drape configured for placement between the tool holder elements and the end effector.

16. The device according to claim 15, wherein the one or more fasteners contact the drape when coupling the corresponding tool holder element to the end effector.

17. The device according to claim 16, wherein the one or more fasteners pierce the drape when coupling the tool holder element to the end effector.

18. The device according to claim 16, wherein the drape defines one or more holes each sized for receiving one of the fasteners.

* * * * *